United States Patent
Wu et al.

(10) Patent No.: US 12,376,922 B2
(45) Date of Patent: Aug. 5, 2025

(54) TOOL HEAD POSTURE ADJUSTMENT METHOD, APPARATUS AND READABLE STORAGE MEDIUM

(71) Applicant: Zhi Mei Kang Min (Zhuhai) Health Tech Co., Ltd., Zhuhai (CN)

(72) Inventors: Chao Wu, Zhuhai (CN); Aizhen Li, Zhuhai (CN)

(73) Assignee: ZHI MEI KANG MIN (ZHUHAI) HEALTH TECH CO., LTD., Zhuhai (CN)

( * ) Notice: Subject to any disclaimer, the term of this patent is extended or adjusted under 35 U.S.C. 154(b) by 113 days.

(21) Appl. No.: 17/906,639

(22) PCT Filed: Dec. 16, 2020

(86) PCT No.: PCT/CN2020/136749
§ 371 (c)(1),
(2) Date: Sep. 19, 2022

(87) PCT Pub. No.: WO2021/184859
PCT Pub. Date: Sep. 23, 2021

(65) Prior Publication Data
US 2024/0261044 A1   Aug. 8, 2024

(30) Foreign Application Priority Data
Mar. 19, 2020 (CN) .......................... 202010194511.7

(51) Int. Cl.
*A61B 34/32* (2016.01)
*A61B 18/06* (2006.01)
(Continued)

(52) U.S. Cl.
CPC .............. *A61B 34/32* (2016.02); *A61B 18/06* (2013.01); *A61H 39/08* (2013.01); *B25J 13/089* (2013.01);
(Continued)

(58) Field of Classification Search
CPC . A61B 34/32; A61B 18/06; A61B 2562/0257; A61H 39/08;
(Continued)

(56) References Cited

U.S. PATENT DOCUMENTS

2017/0348061 A1* 12/2017 Joshi ...................... A61B 90/90
2020/0306780 A1* 10/2020 Maas ..................... B05B 16/20

FOREIGN PATENT DOCUMENTS

CN 103447877 A * 12/2013
CN 103471545 A    12/2013
(Continued)

OTHER PUBLICATIONS

Daoshan OuYang, Hsi-Yung Feng, On the normal vector estimation for point cloud data from smooth surfaces, Computer-Aided Design, vol. 37, Issue 10, 2005, pp. 0010-4485. (Year: 2005).*
(Continued)

*Primary Examiner* — Wade Miles
*Assistant Examiner* — Sidney Leigh Molnar
(74) *Attorney, Agent, or Firm* — Gottlieb, Rackman & Reisman, PC

(57) ABSTRACT

A tool head posture adjustment method and apparatus, and a readable storage medium are disclosed. Distances to laser points are measured by laser distance sensors, and the laser points can construct at least one plane, thereby determining each plane corresponding to a site to be checked; and a comprehensive normal vector of each plane is calculated, and posture parameters of a tool head of a robot are calculated by using a posture expression, thereby adjusting the tool head posture.

8 Claims, 2 Drawing Sheets

(51) Int. Cl.
  *A61H 39/08* (2006.01)
  *B25J 13/08* (2006.01)

(52) U.S. Cl.
  CPC .............. *A61B 2562/0257* (2013.01); *A61H 2201/1659* (2013.01); *A61H 2201/5064* (2013.01); *A61H 2201/5092* (2013.01)

(58) Field of Classification Search
  CPC .... A61H 2201/1659; A61H 2201/5064; A61H 2201/5092; B25J 13/089; B25J 9/1692; B25J 9/1679; B25J 9/1694; B25J 19/022; B25J 9/1664; B25J 13/088; G05B 2219/40613; G05B 2219/37275; G05B 2219/40623; G05B 2219/45122
  USPC .................. 700/245–264; 318/568.11–568.25
  See application file for complete search history.

(56) References Cited

FOREIGN PATENT DOCUMENTS

| | | | | |
|---|---|---|---|---|
| CN | 105091744 A | | 11/2015 | |
| CN | 106965180 A | | 7/2017 | |
| CN | 108177143 A | * | 6/2018 | ............ B25J 9/1697 |
| CN | 108453743 A | | 8/2018 | |
| CN | 108839027 A | * | 11/2018 | ............ B25J 9/1694 |
| CN | 110575386 A | | 12/2019 | |
| CN | 111438689 A | | 7/2020 | |
| KR | 20170058720 A | | 5/2017 | |
| WO | WO-2019101803 A1 | * | 5/2019 | ........... B05B 12/084 |

OTHER PUBLICATIONS

Weisstein, Eric W, "Euler Angles," 2009, From MathWorld—A Wolfram Web Resource. https://mathworld.wolfram.com/EulerAngles.html (Year: 2009).*
Lyryx Learning based on the original text by K. Kuttler, A First Course In Linear Algebra, 2017, Revision A, Chapter 4.4: Length of a Vector (pp. 155-159), Chapter 4.6: Parametric Lines (pp. 161-166). https://lyryx.com/wp-content/uploads/2017/06/Kuttler-LinearAlgebra-AFirstCourse-2017A.pdf (Year: 2017).*
International Search Report for Application No. PCT/CN2020/136749, mailing date Mar. 16, 2021(english translation).
Written Opinion for Application No. PCT/CN2020/136749, mailing date Mar. 16, 2021 (english translation).
International Search Report for Application No. PCT/CN2020/136749, mailing date Mar. 16, 2021(Chinese version).
Written Opinion for Application No. PCT/CN2020/136749, mailing date Mar. 16, 2021(Chinese version).

* cited by examiner

TOOL HEAD POSTURE ADJUSTMENT METHOD, APPARATUS AND READABLE STORAGE MEDIUM

CROSS-REFERENCE TO RELATED APPLICATIONS

This application is a national stage filing under 35 U.S.C. § 371 of international application number PCT/CN2020/136749, filed 16 Dec. 2020, which claims priority to Chinese patent application No. 2020101945117 filed 19 Mar. 2020. The contents of these applications are incorporated herein by reference in their entirety.

TECHNICAL FIELD

The disclosure relates to the technical field of robots, in particular to a tool head posture adjustment method and apparatus, and a readable storage medium.

BACKGROUND

With the development of robot technology, the performance and safety of robots have been greatly improved, and the emergence of robots capable of human-machine cooperation has remarkably made human-robot cooperation be practical. With the rapid development of modern industry in the last decade, a widespread use of robots has also made the cost of robots approach the affordable level of consumers in the last two years. As a kind of robots, the personal care robot includes a tool head with a care function (massage, moxibustion, making up, beautifying, etc.) mounted at an end of the robot arm, and the tool head is in direct contact with the human body to be cared or maintains a specific distance and posture to carry out care work.

At present, the solutions to determine the posture (position and attitude) of a care robot during work mainly include a machine vision solution, a contacting multi-axis force sensor solution, and a radar (ultrasonic or laser, etc.) sensor. The above-mentioned solutions are all imperfect. For example, the robots involved in the machine vision solution are expensive. According to the robot vision solution, a special light source is required to irradiate, scanning time and coordinate generation time are long, real-time performance is poor, the camera with a large volume is not conducive to being integrated in the tool head, and the private parts of clients are exposed. The robots involved in the contacting multi-axis force sensor solution are expensive, which is only adaptable to a scenario where a tool head is in contact with a human body, and has no prospective guidance on the tool head posture. The robots involved in the radar solution are expensive, poor in accuracy, large in blind areas, susceptible to interference, and have a potential risk to human health from the emission of long-term radar waves. Therefore, how to provide a tool head posture determination solution which is low in cost, high in precision, strong in real-time performance and accurate in posture determination has become a problem to be solved.

The above-mentioned content is only used to assist in understanding the technical solutions of the disclosure, and does not represent an admission that the above-mentioned content is the prior art.

SUMMARY

A main object of the disclosure is to provide a tool head posture determination solution which is low in cost, high in precision, strong in real-time performance and accurate in posture determination.

In order to achieve the above object, a tool head posture adjustment method is provided according an embodiment of the disclosure, including:

controlling laser points of laser distance sensors to irradiate onto a site to be checked in a way that the laser points are not on a straight line, where there are more than two of the laser distance sensors;

acquiring a distance measured by each of the laser distance sensors, an initial coordinate of each of the laser distance sensors and a laser direction of each of the laser distance sensors, where the distance is a distance between each laser distance sensor and the corresponding laser point;

calculating a laser point coordinate of each of the laser points on the site to be checked based on the distance, the initial coordinate and the laser direction, and calculating a comprehensive plane normal vector of a plane determined by the laser point coordinates, where the comprehensive plane normal vector is obtained from a plane normal vector of the plane determined by the laser point coordinates; and calculating posture parameters of a tool head posture of the robot to be adjusted based on a preset posture expression, the distances and the comprehensive plane normal vector, and controlling a tool head of the robot to be adjusted to a posture to be adjusted based on the posture parameters.

Optionally, if there are more than three of the laser distance sensors, calculating a comprehensive normal vector of a plane determined by the laser point coordinates includes:

calculating plane normal vectors of corresponding planes determined by the laser point coordinates; and calculating a weighted average value of the plane normal vectors using a weighted average algorithm, and taking the weighted average value as the comprehensive plane normal vector.

Optionally, the posture expression includes an Euler angle, a quaternion, or a rotation matrix expression.

Optionally, there are three of the laser distance sensors, and laser beams of the laser distance sensors are parallel to one another.

Optionally, calculating a laser point coordinate of each of the laser points on the site to be checked based on the distance, the initial coordinate and the laser direction includes:

assuming unit vectors of the laser directions to be $R_a(r_{x1}, r_{y1}, r_{z1})$, $R_b(r_{x2}, r_{y2}, r_{z2})$ and $R_c(r_{x3}, r_{y3}, r_{z3})$ respectively, the coordinates of the laser distance sensors in a tool head coordinate system to be $P_a(x_1, y_1, z_1)$, $P_b(x_2, y_2, z_2)$ and $P_c(x_3, y_3, z_3)$, the distances to be $d_1$, $d_2$ and $d_3$, and the coordinates of the laser points to be $U_a$, $U_b$ and $U_c$, then $$U_{a \cdot x} = x_1 + r_{x1} * d_1, \ U_{a \cdot y} = y_1 + r_{y1} * d_1, \ U_{a \cdot z} = z_1 + r_{z1} * d_1;$$

$$U_{b \cdot x} = x_2 + r_{x2} * d_2, \ U_{b \cdot y} = y_2 + r_{y2} * d_2, \ U_{b \cdot z} = z_2 + r_{z2} * d_2;$$

$$U_{c \cdot x} = x_3 + r_{x3} * d_3, \ U_{c \cdot y} = y_3 + r_{y3} * d_3, \ U_{c \cdot z} = z_3 + r_{z3} * d_3;$$

to obtain the coordinates of the laser points $Ua(U_{a \cdot x}, U_{a \cdot y}, U_{a \cdot z})$, $U_b(U_{b \cdot x}, U_{b \cdot y}, U_{b \cdot z})$ and $Uc(U_{c \cdot x}, U_{c \cdot y}, U_{c \cdot z})$.

Optionally, calculating posture parameters of a tool head posture of the robot to be adjusted based on a preset posture expression, the distances and the comprehensive plane normal vector includes:

assuming the obtained comprehensive plane normal vector to be $V(v_x, v_y, v_z)$, with the convention that $v_z>0$, where if $v_z<0$, the comprehensive plane normal vector is multiplied by $-1$;

presetting a formula $M(\alpha, \beta, \gamma)*[0, 0, 1]^T = V_{norm}^T$, where $M(\alpha, \beta, \gamma)$ is a rotation matrix in an Euler angle rotation formula, where $V_{norm}$ represents the comprehensive plane normal vector with modulo being 1, and $\alpha, \beta$ and $\gamma$ respectively represent Euler angles; and obtaining the posture parameters based on the preset formula, the distances and the Euler angle rotation formula.

Optionally, obtaining the posture parameters based on the preset formula, the distances and the Euler angle rotation formula includes:

assuming $r_x$ to be equal to 0, and calculating $r_y$ and $r_z$ based on the preset formula and the Euler angle rotation formula, where $r_x$, $r_y$ and $r_z$ are Euler angles $\alpha$, $\beta$ and $\gamma$, respectively;

calculating a comprehensive distance using a preset algorithm based on the distances, which is assumed to be $d_{aver}$;

adding $d_{aver}$ to an origin of the tool head coordinate system in z direction so that the origin is set at the site to be checked;

acquiring posture parameters of the origin with respect to a base coordinate system of a manipulator base when the origin is provided at the site to be checked, where the posture parameters are assumed to be $x_0, y_0, z_0, r_{x0}, r_{y0}$ and $r_{z0}$; and assuming Euler angle parameters of the tool head posture to be adjusted to be $R_x$, $R_y$ and $R_z$, then $R_x = r_{x0}$, $R_y = r_{y0} + r_y$, and $R_z = r_{z0} + r_z$, then the posture parameters of the tool head posture to be adjusted being $x_0, y_0, z_0, R_x, R_y$ and $R_z$.

Optionally, the preset algorithm includes an average algorithm and a weighted average algorithm.

Further, in order to achieve the above object, a tool head posture adjustment apparatus is provided according an embodiment of the disclosure, including: a memory, a processor, and a tool head posture adjustment program stored on the memory and executable by the processor, when executed by the processor, the tool head posture adjustment program implements the method as described above.

Further, in order to achieve above object, a readable storage medium is provided according an embodiment of the disclosure, storing thereon a tool head posture adjustment program which, when executed by a processor, implements the tool head posture adjustment method as described above.

A tool head posture adjustment method and apparatus, and a readable storage medium are provided according an embodiment of the disclosure, which can accurately determine the tool head posture of a robot, thereby improving the working efficiency of the robot. According to the disclosure, the laser distance sensors are low in cost, small in size and high in accuracy, can be well integrated with the tool head of a robot, so as to facilitate the determination of the tool head posture, can adjust the positions of the laser distance sensors in real time. The disclosure can adapt to a scenario where a tool head is in contact with a human body or a scenario where the tool head is kept at a certain distance from the human body.

The objects, features and advantages of the disclosure will be further described with reference to the accompanying drawings in conjunction with the embodiments.

DETAILED DESCRIPTION

In order to make the purpose, technical solutions and advantages of the disclosure clearer, the disclosure will be described in further detail below in conjunction with the accompanying drawings and embodiments. It should be understood that the specific embodiments described herein are only used to explain the disclosure and not intended to limit the disclosure.

Figure 1:
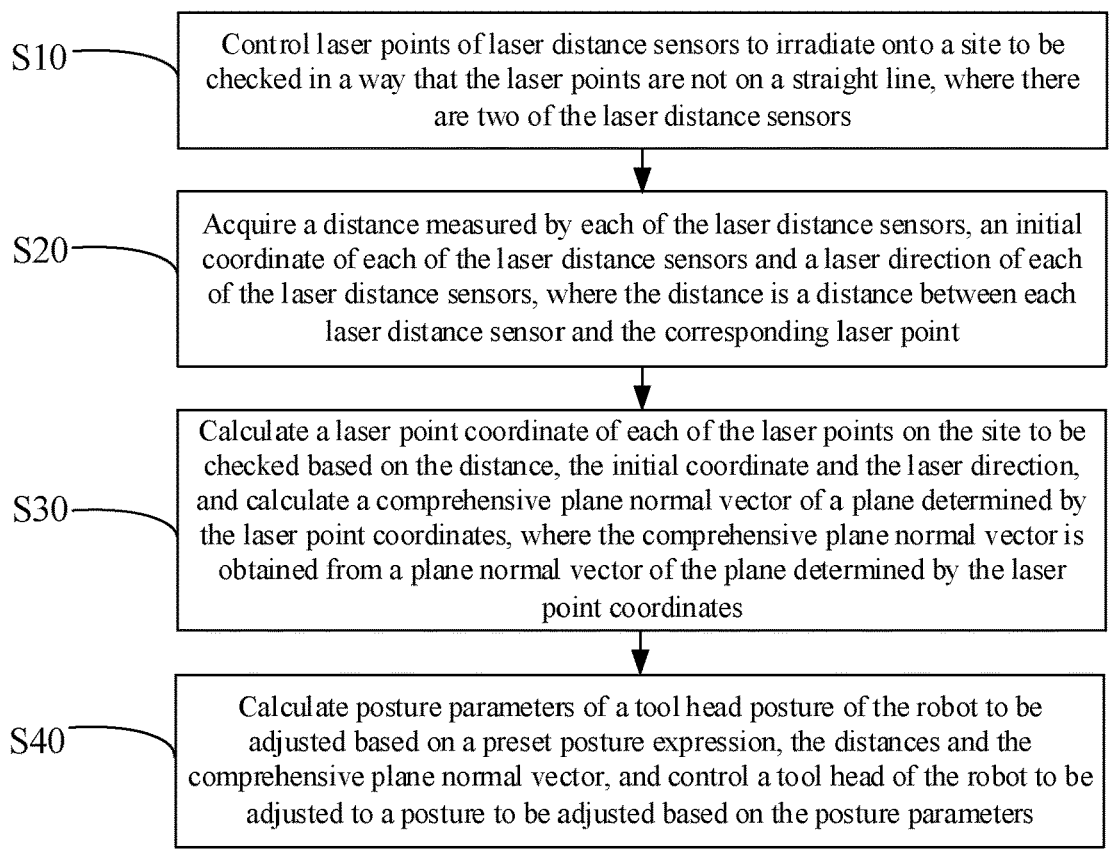
FIG. 1 is a schematic flowchart of a tool head posture adjustment method according to a first embodiment of the disclosure.

A tool head posture adjustment method is provided according an embodiment of the disclosure. Referring to FIG. 1, which is a schematic flowchart of a tool head posture adjustment method according to a first embodiment of the disclosure.

In the present embodiment, the tool head posture adjustment method is executed by a tool head posture adjustment system, which includes a tool head posture adjustment apparatus, and the tool head posture adjustment apparatus may be a robot device, such as a moxibustion instrument and a massage instrument, but may also be a terminal device, such as a PC and a palmtop computer. According to the disclosure, distances to laser points are measured by laser distance sensors, and the various laser points can construct at least one plane, thereby determining each plane corresponding to a site to be checked; and a comprehensive normal vector of the planes is calculated, and posture parameters of a tool head of a robot are calculated by using a posture expression, thereby adjusting the tool head posture. According to the tool head posture adjustment method and apparatus, posture parameters of a tool head posture to be adjusted can be accurately determined. The present embodiment takes the moxibustion instrument as an example for illustration. The tool head posture adjustment method includes the following steps.

At S10, laser points of laser distance sensors are controlled to irradiate onto a site to be checked in a way that the laser points are not on a straight line, where the number of the laser distance sensors is more than 2.

Figure 2:
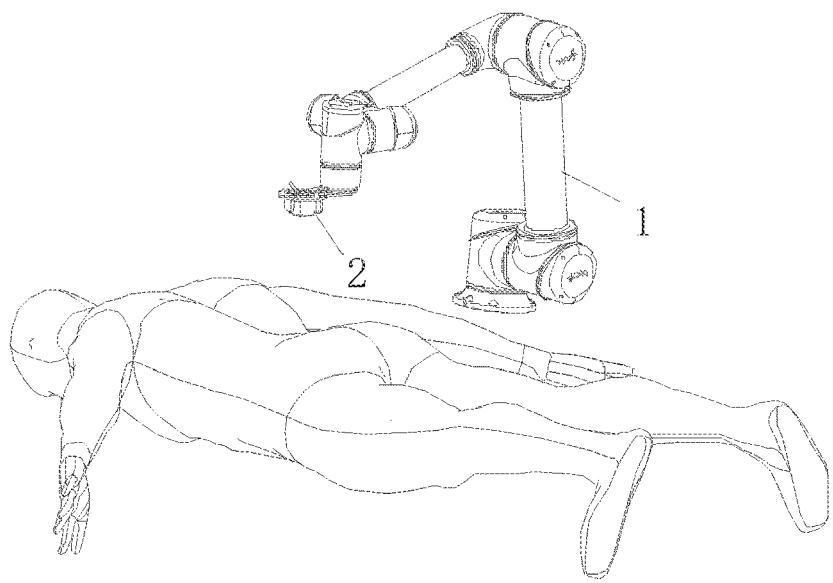
FIG. 2 is a schematic view of the moxibustion instrument robot performing acupuncture on a site to be checked.

In the present embodiment, referring to FIG. 2, which is a schematic view of the moxibustion instrument robot carrying out acupuncture at a site to be checked, where the site to be checked includes a body site of a patient to be acupunctured, and the laser distance sensors may be mounted on a tool head of the moxibustion instrument robot, for example, three or more laser distance sensors 2 are mounted on a face of the robot tool head having a fixed linkage relationship, and certainly, can also be mounted on other parts of the robot. A manipulator 1 is used to adjust the tool head posture. When the site to be checked enters the range of the distance from the laser distance sensors 2, laser beams of the respective laser distance sensors 2 irradiate onto the site to be checked, forming laser points at the site to be checked, the number of the laser distance sensors 2 is more than or equal to 3. Since the laser points must be able to construct a plane, the laser points cannot be on the same straight line. Preferably, the laser beams of the laser distance sensor 2 are prevented from converging at a point, and the laser beams are parallel to each other and never have an intersection point, so that the algorithm can be simplified when calculating the coordinates of the laser points, thereby improving the efficiency of data processing and further improving the efficiency of adjusting the tool head posture.

At S20, a distance measured by each of the laser distance sensors, an initial coordinate of each of the laser distance sensors and a laser direction of each of the laser distance sensors are acquired, where the distance is a distance between each laser distance sensor and the corresponding laser point.

In the present embodiment, the laser distance sensors 2 can measure a distance to a laser point, set a tool head coordinate system, and acquire initial coordinates of the laser distance sensors 2 in the tool head coordinate system and laser directions of the laser distance sensors 2, where the laser directions of the laser distance sensors 2 can be represented by a unit vector.

At S30, a laser point coordinate of each of the laser points on the site to be checked is calculated based on the distance, the initial coordinate and the laser direction, and a comprehensive plane normal vector of a plane determined by the laser point coordinates are calculated, where the comprehensive plane normal vector is obtained from a plane normal vector of a plane determined by the laser point coordinates.

Figure 3:
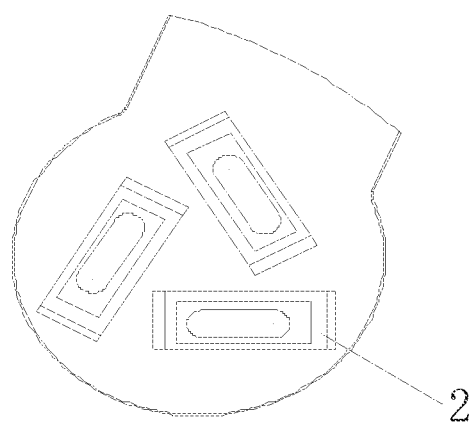
FIG. 3 is a schematic view of three laser distance sensors on the tool head in the first embodiment.

In the present embodiment, referring to FIG. 3, which is a schematic diagram of three laser distance sensors 2 on the tool head, if there are three laser distance sensors 2, the comprehensive plane normal vector is a plane normal vector of the plane where the three laser points are located, where the plane normal vector may be obtained by vector cross multiplication. If there are more than three laser distance sensors 2, the comprehensive normal vector may be a normal vector obtained using a weighted average algorithm or other algorithms. For example, if the laser points can construct four planes, the normal vectors of the four planes are respectively calculated by vector cross multiplication, and then a weighted average value of the four normal vectors is calculated by a weighted average algorithm, thereby obtaining a comprehensive normal vector.

If the number of the laser distance sensors 2 is 3, the laser beams of the laser distance sensors 2 are parallel to each other, unit vectors of the respective laser directions are set as $R_a(r_{x1}, r_{y1}, r_{z1})$, $R_b(r_{x2}, r_{y2}, r_{z2})$ and $R_c(r_{x3}, r_{y3}, r_{z3})$, respectively, the coordinates of the laser distance sensors in the tool head coordinate system are set as $P_a(x_1, y_1, z_1)$, $P_b(x_2, y_2, z_2)$ and $P_c(x_3, y_3, z_3)$, the respective distances are set as $d_1$, $d_2$ and $d_3$, and the coordinates of the laser points are set as $U_a$, $U_b$ and $U_c$, then $$U_{a \cdot x} = x_1 + r_{x1} * d_1, \ U_{a \cdot y} = y_1 + r_{y1} * d_1, \ U_{a \cdot z} = z_1 + r_{z1} * d_1;$$

$$U_{b \cdot x} = x_2 + r_{x2} * d_2, \ U_{b \cdot y} = y_2 + r_{y2} * d_2, \ U_{b \cdot z} = z_2 + r_{z2} * d_2;$$

$$U_{c \cdot x} = x_3 + r_{x3} * d_3, \ U_{c \cdot y} = y_3 + r_{y3} * d_3, \ U_{c \cdot z} = z_3 + r_{z3} * d_3;$$

that is, the coordinates $U_a$ ($U_{a \cdot x}$, $U_{a \cdot y}$, $U_{a \cdot z}$), $U_b$ ($U_{b \cdot x}$, $U_{b \cdot y}$, $U_{b \cdot z}$) and $U_c$ ($U_{c \cdot x}$, $U_{c \cdot y}$, $U_{c \cdot z}$) of the laser points are obtained, and the plane normal vector of the three laser points may be calculated by vector cross multiplication.

At S40, posture parameters of a tool head posture of the robot to be adjusted are calculated based on a preset posture expression, the distances and the comprehensive plane normal vectors, and the tool head of the robot to be adjusted is controlled to the posture to be adjusted based on the posture parameters.

In the present embodiment, the preset posture expression includes expressions such as an Euler angle, a quaternion or a rotation matrix, and the posture parameters of the posture of the robot to be adjusted are obtained by using the posture expression according to the comprehensive plane normal vector and the distances.

The Euler angle rotation formula is used to calculate the posture parameters of the posture of the robot to be adjusted hereinafter.

The obtained comprehensive plane normal vector is assumed to be $V(v_x, v_y, v_z)$, with the convention that $v_z > 0$, where if $v_z < 0$, the comprehensive plane normal vector is multiplied by $-1$, which is to calculate the unit normal vector of the comprehensive plane normal vector, so as to determine the direction of the comprehensive normal vector.

The Euler angle rotation formula is:

$$M(\alpha, \beta, \gamma) = \begin{bmatrix} \cos\gamma\cos\gamma - \cos\beta\sin\alpha\sin\gamma & -\cos\beta\cos\gamma\sin\alpha - \cos\alpha\sin\gamma & \sin\alpha\sin\beta \\ \cos\gamma\sin\alpha + \cos\alpha\cos\beta\sin\lambda & \cos\alpha\cos\beta\cos\gamma - \sin\alpha\sin\lambda & -\cos\alpha\sin\beta \\ \sin\beta\sin\lambda & \cos\gamma\sin\beta & \cos\beta \end{bmatrix}$$

Assuming the preset formula $M(\alpha, \beta, \gamma)*[0, 0, 1]^T = V_{norm}^T$, where $M(\alpha, \beta, \gamma)$ is a rotation matrix in the Euler angle rotation formula, $\alpha$, $\beta$, and $\gamma$ respectively represent Euler angles, $V_{norm}$ represents the comprehensive plane normal vector with modulo being 1, and $\alpha$, $\beta$ and $\gamma$ respectively represent Euler angles.

Let $r_x$ to be equal to 0, $r_y$ and $r_z$ are obtained based on the preset formula and the Euler angle rotation formula, where $r_x$, $r_y$ and $r_z$ are Euler angles $\alpha$, $\beta$ and $\gamma$, respectively, a comprehensive distance is calculated using a preset algorithm based on a distance, and is set as $d_{aver}$; $d_{aver}$ is added to an origin of a tool head coordinate system in a z direction so that the origin is set at a site to be checked; then posture parameters of the origin with respect to a base coordinate system of a manipulator base are acquired when the origin is provided at the site to be checked, and the posture parameters are set as $x_0$, $y_0$, $z_0$, $r_{x0}$, $r_{y0}$ and $r_{z0}$; and the Euler angle parameters of the tool head posture to be adjusted are set as $R_x$, $R_y$ and $R_z$, then $R_x = r_{x0}$, $R_y = r_{y0} + r_y$, and $R_z = r_{z0} + r_z$, then the posture parameters of the tool head posture to be adjusted are $x_0$, $y_0$, $z_0$, $R_x$, $R_y$ and $R_z$, where the preset algorithm includes an average algorithm and a weighted average algorithm, for example, an average value of $d_1$, $d_2$ and $d_3$ is calculated using the average algorithm to obtain $d_{aver}$.

The tool head posture is adjusted according to the posture parameters of the posture to be adjusted, so that the robot can accurately perform acupuncture and moxibustion care on the site to be checked.

The present embodiment provides a tool head posture adjustment method, including: controlling laser points of laser distance sensors to irradiate onto a site to be checked in a way that the laser points are not on a straight line, where the number of the laser distance sensors is more than 2; acquiring a distance measured by each of the laser distance sensors, an initial coordinate of each of the laser distance sensors and a laser direction of each of the laser distance sensors, where the distance is a distance between each laser distance sensor and the corresponding laser point; calculating a laser point coordinate of each of the laser points on the site to be checked based on the distance, the initial coordinate and the laser direction, and calculating a comprehensive plane normal vector of a plane determined by the laser point coordinates, where the comprehensive plane normal vector is obtained from a plane normal vector of the plane determined by the laser point coordinates; and calculating posture parameters of a tool head posture of the robot to be adjusted based on a preset posture expression, the distances and the comprehensive plane normal vector, and controlling the tool head of the robot to be adjusted to the posture to be adjusted based on the posture parameters. In this way, the posture parameters of the tool head posture to be adjusted can be accurately determined, thereby improving the operation efficiency of the moxibustion instrument. In addition, the laser distance sensors according to an embodiment of the disclosure are low in cost, high in precision and strong in real-time performance when the robot works, and can adapt to a scenario where a tool head is in contact with a human body or a scenario where the tool head is kept at a certain distance from the human body.

In addition, a readable storage medium is provided according an embodiment of the disclosure. The readable storage medium stores thereon a tool head posture adjustment program, which, when executed by a processor, implements the following steps:

controlling laser points of laser distance sensors to irradiate onto a site to be checked in a way that the laser points are not on a straight line, where the number of the laser distance sensors is more than 2;

acquiring a distance measured by each of the laser distance sensors, an initial coordinate of each of the laser distance sensors and a laser direction of each of the laser distance sensors, where the distance is a distance between each laser distance sensor and the corresponding laser point;

calculating a laser point coordinate of each of the laser points on the site to be checked based on the distance, the initial coordinate and the laser direction, and calculating a comprehensive plane normal vector of a plane determined by the laser point coordinates, where the comprehensive plane normal vector is obtained from a plane normal vector of the plane determined by the laser point coordinates; and calculating posture parameters of a tool head posture of the robot to be adjusted based on a preset posture expression, the distances and the comprehensive plane normal vector, and controlling a tool head of the robot to be adjusted to a posture to be adjusted based on the posture parameters.

Further, if there are more than three of the laser distance sensors, calculating a comprehensive normal vector of a plane determined by the laser point coordinates includes:

calculating plane normal vectors of corresponding planes determined by the laser point coordinates; and calculating a weighted average value of the plane normal vectors using a weighted average algorithm, and taking the weighted average value as the comprehensive plane normal vector.

Further, the posture expression includes an Euler angle, a quaternion, or a rotation matrix expression.

Further, there are three of the laser distance sensors, and laser beams of the laser distance sensors are parallel to one another.

Further, calculating a laser point coordinate of each of the laser points on the site to be checked based on the distance, the initial coordinate and the laser direction includes:

assuming unit vectors of the laser directions to be $R_a(r_{x1}, r_{y1}, r_{z1})$, $R_b(r_{x2}, r_{y2}, r_{z2})$ and $R_c(r_{x3}, r_{y3}, r_{z3})$ respectively, the coordinates of the laser distance sensors in a tool head coordinate system to be $P_a(x_1, y_1, z_1)$, $P_b(x_2, y_2, z_2)$ and $P_c(x_3, y_3, z_3)$, the distances to be $d_1$, $d_2$ and $d_3$, and the coordinates of the laser points to be $U_a$, $U_b$ and $U_c$, then $$U_{a \cdot x} = x_1 + r_{x1} * d_1, \; U_{a \cdot y} = y_1 + r_{y1} * d_1, \; U_{a \cdot z} = z_1 + r_{z1} * d_1;$$

$$U_{b \cdot x} = x_2 + r_{x2} * d_2, \; U_{b \cdot y} = y_2 + r_{y2} * d_2, \; U_{b \cdot z} = z_2 + r_{z2} * d_2;$$

$$U_{c \cdot x} = x_3 + r_{x3} * d_3, \; U_{c \cdot y} = y_3 + r_{y3} * d_3, \; U_{c \cdot z} = z_3 + r_{z3} * d_3;$$

to obtain the coordinates of the laser points, where $P_a$, $P_b$ and $P_c$ are respectively the coordinates $Ua(U_{a \cdot x}, U_{a \cdot y}, U_{a \cdot z})$, $U_b(U_{b \cdot x}, U_{b \cdot y}, U_{b \cdot z})$ and $Uc(U_{c \cdot x}, U_{c \cdot y}, U_{c \cdot z})$ of the laser distance sensors.

Further, calculating posture parameters of a tool head posture of the robot to be adjusted based on a preset posture expression, the distances and the comprehensive plane normal vector includes:

assuming the obtained comprehensive plane normal vector to be $V(v_x, v_y, v_z)$, with the convention that $v_z > 0$, where if $v_z < 0$, the comprehensive plane normal vector is multiplied by $-1$;

presetting a formula $M(\alpha, \beta, \gamma)*[0, 0, 1]^T = V_{norm}^T$, where $M(\alpha, \beta, \gamma)$ is a rotation matrix in an Euler angle rotation formula; and obtaining the posture parameters based on the preset formula, the distances and the Euler angle rotation formula, where $V_{norm}$ represents the comprehensive plane normal vector with modulo being 1, and $\alpha$, $\beta$ and $\gamma$ respectively represent Euler angles.

Further, obtaining the posture parameters based on the preset formula, the distances and the Euler angle rotation formula includes:

assuming $r_x$ to be equal to 0, and calculating $r_y$ and $r_z$ based on the preset formula and the Euler angle rotation formula, where $r_x$, $r_y$ and $r_z$ are Euler angles $\alpha$, $\beta$ and $\gamma$, respectively;

calculating a comprehensive distance using a preset algorithm based on the distances, which is assumed to be $d_{aver}$;

adding $d_{aver}$ to an origin of the tool head coordinate system in z direction so that the origin is set at the site to be checked;

acquiring posture parameters of the origin with respect to a base coordinate system of a manipulator base when the origin is provided at the site to be checked, where the posture parameters are assumed to be $x_0$, $y_0$, $z_0$, $r_{x0}$, $r_{y0}$ and $r_{z0}$; and assuming Euler angle parameters of the tool head posture to be adjusted to be $R_x$, $R_y$ and $R_z$, then $R_x = r_{x0}$, $R_y = r_{y0} + r_y$, and $R_z = r_{z0} + r_z$, then the posture parameters of the tool head posture to be adjusted being $x_0$, $y_0$, $z_0$, $R_x$, $R_y$ and $R_z$.

Further, the preset algorithm includes an average algorithm and a weighted average algorithm.

It should be noted that, as used herein, the terms "comprising", "including" or any other variation thereof are intended to encompass non-exclusive inclusion, such that a process, method, article or system including a series of elements includes not only those elements, but also other elements that are not explicitly listed, or also includes elements inherent to such a process, method, article, or system. Without further limitation, an element defined by the statement "includes a . . . " does not preclude the existence of additional identical elements in the process, method, article or system that includes the element.

The above-mentioned serial numbers of the embodiments of the disclosure are merely for the purpose of description and do not represent the advantages and disadvantages of the embodiments.

From the description of the embodiments given above, it will be clear to a person of ordinary skill in the art that the method of the embodiments described above can be implemented by software plus a necessary general hardware platform, and certainly also by hardware, but in many cases the former is a better way. Based on such understanding, the technical solutions of the disclosure essentially or the part that contributes to the prior art can be reflected in the form of software products, and the computer software products are stored in a storage medium (such as an ROM/RAM, a magnetic diskette and an optical disk) as described above, and include several instructions for making a terminal device (which may be a mobile phone, a computer, a server, an air conditioner, or a network device, etc.) to execute the method according to various embodiments of the disclosure.

The above are only preferred embodiments of the disclosure, and do not therefore limit the patent scope of the disclosure. All equivalent structures or equivalent process changes made by using the description of the disclosure and the accompanying drawings, or directly or indirectly used in other related technical fields, are equally included in the scope of patent protection of the disclosure.

The invention claimed is:

1. A tool head posture adjustment method, applicable to a robot, comprising:
controlling laser points of laser distance sensors to irradiate onto a site in a way that the laser points are not on a straight line, where there are more than two of the laser distance sensors;
acquiring a distance measured by each of the laser distance sensors, an initial coordinate of each of the laser distance sensors and a laser direction of each of the laser distance sensors, where the distance is a distance between each laser distance sensor and the corresponding laser point;
calculating a laser point coordinate of each of the laser points on the site based on the distance, the initial coordinate and the laser direction, and calculating a comprehensive plane normal vector of a plane determined by the laser point coordinates, where the comprehensive plane normal vector is obtained from a plane normal vector of the plane determined by the laser point coordinates; and
calculating posture parameters of a tool head posture of the robot to be adjusted based on a preset posture expression, the distances and the comprehensive plane normal vector, and controlling a tool head of the robot to be adjusted to an adjusted posture based on the posture parameters;
wherein the posture expression comprises an Euler angle, a quaternion, or a rotation matrix expression, and calculating posture parameters of the tool head posture of the robot to be adjusted based on a preset posture expression, the distances and the comprehensive plane normal vector comprises:
assuming the obtained comprehensive plane normal vector to be $V(v_x, v_y, v_z)$, with the convention that $v_z>0$, where when $v_z<0$, the comprehensive plane normal vector is multiplied by $-1$;
presetting a formula $M(\alpha, \beta, \gamma)*[0, 0, 1]^T = V_{norm}^T$, where $M(\alpha, \beta, \gamma)$ is a rotation matrix in an Euler angle rotation formula, where $V_{norm}$ represents the comprehensive plane normal vector with modulo being 1, and $\alpha$, $\beta$ and $\gamma$ respectively represent Euler angles, and
obtaining the posture parameters based on the preset formula, the distances and the Euler angle rotation formula.

2. The tool head posture adjustment method according to claim 1, wherein when there are more than three of the laser distance sensors, calculating a comprehensive normal vector of a plane determined by the laser point coordinates comprises:
calculating plane normal vectors of corresponding planes determined by the laser point coordinates; and
calculating a weighted average value of the plane normal vectors using a weighted average algorithm, and taking the weighted average value as the comprehensive plane normal vector.

3. The tool head posture adjustment method according to claim 1, wherein there are three of the laser distance sensors, and laser beams of the laser distance sensors are parallel to one another.

4. The tool head posture adjustment method according to claim 3, wherein calculating a laser point coordinate of each of the laser points on the site based on the distance, the initial coordinate and the laser direction comprises:
assuming unit vectors of the laser directions to be $R_a(r_{x1}, r_{y1}, r_{z1})$, $R_b(r_{x2}, r_{y2}, r_{z2})$ and $R_c(r_{x3}, r_{y3}, r_{z3})$ respectively, the coordinates of the laser distance sensors in a tool head coordinate system to be $P_a(x_1, y_1, z_1)$, $P_b(x_2, y_2, z_2)$ and $P_c(x_3, y_3, z_3)$, the distances to be $d_1$, $d_2$ and $d_3$, and the coordinates of the laser points to be $U_a$, $U_b$ and $U_c$, then $$U_{a \cdot x} = x_1 + r_{x1}*d_1, U_{a \cdot y} = y_1 + r_{y1}*d_1, U_{a \cdot z} = z_1 + r_{z1}*d_1;$$

$$U_{b \cdot x} = x_2 + r_{x2}*d_2, U_{b \cdot y} = y_2 + r_{y2}*d_2, U_{b \cdot z} = z_2 + r_{z2}*d_2;$$

$$U_{c \cdot x} = x_3 + r_{x3}*d_3, U_{c \cdot y} = y_3 + r_{y3}*d_3, U_{c \cdot z} = z_3 + r_{z3}*d_3;$$

to obtain the coordinates of the laser points $Ua(U_{a \cdot x}, U_{a \cdot y}, U_{a \cdot z})$, $U_b(U_{b \cdot x}, U_{b \cdot y}, U_{b \cdot z})$ and $Uc(U_{c \cdot x}, U_{c \cdot y}, U_{c \cdot z})$.

5. The tool head posture adjustment method according to claim 1, wherein obtaining the posture parameters based on the preset formula, the distances and the Euler angle rotation formula comprises:
assuming $r_x$ to be equal to 0, and calculating $r_y$ and $r_z$ based on the preset formula and the Euler angle rotation formula, where $r_x$, $r_y$ and $r_z$ are Euler angles $\alpha$, $\beta$ and $\gamma$, respectively;
calculating a comprehensive distance using a preset algorithm based on the distances, which is assumed to be $d_{aver}$;
adding $d_{aver}$ to an origin of the tool head coordinate system in z direction so that the origin is set at the site;
acquiring posture parameters of the origin with respect to a base coordinate system of a manipulator base when the origin is provided at the site, where the posture parameters are assumed to be $x_0, y_0, z_0, r_{x0}, r_{y0}$ and $r_{z0}$; and
assuming Euler angle parameters of the tool head posture to be adjusted to be $R_x$, $R_y$ and $R_z$, then $R_x = r_{x0}$, $R_y = r_{y0}+r_y$, and $R_z = r_{z0}+r_z$, then the posture parameters of the tool head posture to be adjusted being $x_0, y_0, z_0, R_x, R_y$ and $R_z$.

6. The tool head posture adjustment method according to claim 5, wherein the preset algorithm comprises an average algorithm and a weighted average algorithm.

7. A tool head posture adjustment apparatus, comprising: a memory, a processor, and a tool head posture adjustment program stored on the memory and executable by the processor, when executed by the processor, the tool head posture adjustment program implements a tool head posture adjustment method, applicable to a robot, comprising:

controlling laser points of laser distance sensors to irradiate onto a site in a way that the laser points are not on a straight line, where there are more than two of the laser distance sensors;

acquiring a distance measured by each of the laser distance sensors, an initial coordinate of each of the laser distance sensors and a laser direction of each of the laser distance sensors, where the distance is a distance between each laser distance sensor and the corresponding laser point;

calculating a laser point coordinate of each of the laser points on the site based on the distance, the initial coordinate and the laser direction, and calculating a comprehensive plane normal vector of a plane determined by the laser point coordinates, where the comprehensive plane normal vector is obtained from a plane normal vector of the plane determined by the laser point coordinates; and calculating posture parameters of a tool head posture of the robot to be adjusted based on a preset posture expression, the distances and the comprehensive plane normal vector, and controlling a tool head of the robot to be adjusted to the adjusted posture based on the posture parameters, wherein the posture expression comprises an Euler angle, a quaternion, or a rotation matrix expression, and calculating posture parameters of the tool head posture of the robot to be adjusted based on a preset posture expression, the distances and the comprehensive plane normal vector comprises;

assuming the obtained comprehensive plane normal vector to be $V(v_x, v_y, v_z)$, with the convention that $v_z>0$, where when $v_z<0$, the comprehensive plane normal vector is multiplied by $-1$;

presetting a formula $M(\alpha, \beta, \gamma)*[0, 0, 1]^T=V_{norm}^T$, where $M(\alpha, \beta, \gamma)$ is a rotation matrix in an Euler angle rotation formula, where $V_{norm}$ represents the comprehensive plane normal vector with modulo being 1, and $\alpha$, $\beta$ and $\gamma$ respectively represent Euler angles, and obtaining the posture parameters based on the preset formula, the distances and the Euler angle rotation formula.

8. A non-transitory computer readable storage medium, storing thereon a tool head posture adjustment program, which, when executed by a processor, implements a tool head posture adjustment method, applicable to a robot, comprising:

controlling laser points of laser distance sensors to irradiate onto a site in a way that the laser points are not on a straight line, where there are more than two of the laser distance sensors;

acquiring a distance measured by each of the laser distance sensors, an initial coordinate of each of the laser distance sensors and a laser direction of each of the laser distance sensors, where the distance is a distance between each laser distance sensor and the corresponding laser point;

calculating a laser point coordinate of each of the laser points on the site based on the distance, the initial coordinate and the laser direction, and calculating a comprehensive plane normal vector of a plane determined by the laser point coordinates, where the comprehensive plane normal vector is obtained from a plane normal vector of the plane determined by the laser point coordinates; and calculating posture parameters of a tool head posture of the robot to be adjusted based on a preset posture expression, the distances and the comprehensive plane normal vector, and controlling a tool head of the robot to be adjusted to an adjusted posture based on the posture parameters;

wherein the posture expression comprises an Euler angle, a quaternion, or a rotation matrix expression, and calculating posture parameters of the tool head posture of the robot to be adjusted based on a preset posture expression, the distances and the comprehensive plane normal vector comprises;

assuming the obtained comprehensive plane normal vector to be $V(v_x, v_y, v_z)$, with the convention that $v_z>0$, where when $v_z<0$, the comprehensive plane normal vector is multiplied by $-1$;

presetting a formula $M(\alpha, \beta, \gamma)*[0, 0, 1]^T=V_{norm}^T$, where $M(\alpha, \beta, \gamma)$ is a rotation matrix in an Euler angle rotation formula, where $V_{norm}$ represents the comprehensive plane normal vector with modulo being 1, and $\alpha$, $\beta$ and $\gamma$ respectively represent Euler angles, and obtaining the posture parameters based on the preset formula, the distances and the Euler angle rotation formula.

\* \* \* \* \*